United States Patent [19]

Giuliano et al.

[11] Patent Number: 5,093,254

[45] Date of Patent: Mar. 3, 1992

[54] AQUEOUS TWO-PHASE PROTEIN EXTRACTION

[75] Inventors: Kenneth A. Giuliano, Pittsburgh, Pa.; David C. Szlag, Boulder, Colo.

[73] Assignee: The United States of America, as represented by the Secretary of Commerce, Washington, D.C.

[21] Appl. No.: 468,651

[22] Filed: Jan. 23, 1990

[51] Int. Cl.$^5$ .............................................. C07K 3/12
[52] U.S. Cl. ...................................... 435/183; 435/190; 435/814; 435/816; 210/511; 210/634; 210/767; 422/256; 530/350; 530/412; 530/421; 530/422; 530/423
[58] Field of Search ............... 530/422, 423, 421, 412, 530/350; 435/183, 190, 814; 422/256; 210/511, 634, 767

[56] References Cited

U.S. PATENT DOCUMENTS

| | | | |
|---|---|---|---|
| 4,427,681 | 1/1984 | Munshi | 514/289 |
| 4,579,661 | 4/1986 | Gustafsson et al. | 210/635 |
| 4,645,829 | 2/1987 | Ho | 530/344 |
| 4,684,723 | 8/1987 | Dove et al. | 530/351 |
| 4,690,892 | 9/1987 | Ananthapadmanabhan et al. | 530/422 |
| 4,716,219 | 12/1987 | Eggimann et al. | 530/413 |

OTHER PUBLICATIONS

Axelsson et al., Eur. J. Biochem., vol. 71, pp. 419–423 (1976).
Szlag et al., Biotechnol. Tech., vol. 2, No. 4, pp. 277–282 (1988).
Szlag et al., Abstr. Pap. Am. Chem. Soc. (195 Meet, IAEC 193), 1988.
Mattiasson et al., ACS Symposium Ser.-Separation, Recovery & Purification in Biotechnology, No. 314, pp. 78–92 (1986).
Park et al., J. Food Sci., vol. 53 (1), pp. 1–3, (1988).
Walter et al., "Partitioning in Aqueous Two-Phase Systems-Therory, Methods, Uses and Applications to Biotechnology", 1985, pp. 608–609.
Kroner et al., "Evaluation of Crude Dextran as Phase--Forming Polymer . . ." Biotechnology and Bioengineering, vol. XXIV, pp. 1015–1045 (1982).
Albertsson, "Partition of Cell Particles and Macromolecules" (3rd Ed.), p. 317 (1985).
Tjerneld et al., "Affinity Liquid-Liquid Extraction of Lactate Dehydrogenase on a Large Scale," Biotechnology and Bioengineering, vol. 30, pp. 309–816 (1987).
Kula et al., "Purification of Enzymes by Liquid-Liquid Extraction," Adv. Biochem. Eng. 24, 1982, pp. 73–118.

Primary Examiner—F. T. Moezie
Assistant Examiner—Andrew G. Rozycki
Attorney, Agent, or Firm—I. William Millen

[57] ABSTRACT

An aqueous two-phase protein partitioning system is disclosed which employs polyvinylpyrrolidone as the upper phase and maltodextrin as the lower phase and provides a low-cost system for protein partitioning. The system can also be employed with the amion derivatives of chlorotriazine dyes, which bind in a noncovalent manner with the PVP and serve as a ligand for the proteins to be separated.

9 Claims, 4 Drawing Sheets

AQUEOUS TWO-PHASE PROTEIN EXTRACTION

BACKGROUND OF THE INVENTION

This invention relates to liquid two-phase extraction systems, particularly, to systems for the affinity partitioning of proteins. This invention also relates to a method of separating proteins using a two-phase protein extraction system.

Aqueous two-phase affinity partitioning methods have been described for the separation of macromolecules such as proteins and nucleic acids, cell particles, and intact cells on a large scale. These types of systems are described, e.g., in Albertsson, Partition of Cell Particles and Macromolecules, John Wiley and Sons, New York, 1986; and Walters et al., Partitioning in Aqueous Two Phase Systems, Academic Press, Inc., 1985.

Partition of enzymes and other proteins between two liquid aqueous phases can be strongly influenced by specific or group specific ligands bound to a water-soluble polymer. A protein ligand covalently attached to a phase-forming polymer can cause that ligand to predominately partition into one of the phases. Affinity partitioning occurs when the partition characteristics of protein are altered due to the interaction of the protein with its asymmetrically partitioned ligand.

Several low cost two-phase systems are known which can handle protein separations on a large scale. These systems use polyethylene glycol (PEG) as the upper phase-forming polymer and crude dextran (as disclosed in Kroner et al., Biotechnology Bioengineering, 24, 1015-1045, 1982), a concentrated salt solution (as disclosed in Kula et al., Adv. Biochem. Bioeng. 24, 73-118, 1982) or hydroxypropyl starch as disclosed in Tjerneld et al., Biotechnology Bioengineering 30, 809-816, 1987, as the lower phase-forming polymer. Two of these systems, the PEG/salt and PEG-crude dextran are seldom used for affinity partitioning. Affinity partitioning cannot take place efficiently in a PEG/salt system due to the effects of the high salt concentrations, whereas the high viscosity of the PEG/crude dextran and/or high cost of fractionated dextran system makes large scale separations difficult.

One of the most successful systems for affinity partitioning thus far on a large scale is the PEG/hydroxypropyl starch system using textile dyes that are covalently bonded to PEG as affinity ligands. Affinity partitioning in the PEG/dextran system is carried out by coupling monochloro-triazine textile dyes to the upper phase polymer (PEG). It utilizes a protein-ligand (i.e., substrate analog, antibody, or textile dye) that is covalently coupled to one of the phase-forming polymers to ensure that the ligand is partitioned predominately into one phase. Although triazine dyes covalently coupled to PEG can be produced on a large scale, the process requires a chromatographic step and several organic solvent extractions in order to produce an effective affinity ligand. To optimize a particular affinity partitioning system, the dye type and other PEG bound ligands need to be empirically tested.

The patent literature also discusses various methods of two-phase aqueous partitioning.

U.S. Pat. No. 4,684,723 discloses a method for separating and recovering proteins from an aqueous system containing one or more therapeutically active proteins or nucleic acids and a polymer component, preferably PEG, having the ability to create two liquid phases within the liquid system. In this method, a water-soluble inorganic salt is added to the aqueous system thereby separating the system into two or more liquid phases. Such separated phases may be selectively enriched in components of the original aqueous system having differing solubilities in the two resultant liquid phases.

U.S. Pat. No. 4,579,661 discloses purification of a biologically active substance with the aid of a system having at least two immiscible aqueous phases. In the process, insoluble particles, e.g., PEG particles, having an affinity for the biologically active substance and a high coefficient of distribution for one of the aqueous phases are used as ligands to bind the substance. Subsequently, the biologically active substance is liberated from the particles after separating the particle-containing phase from one or more other phases.

U.S. Pat. No. 4,645,929 discloses a method of separating polypeptide fractions of a mixed solution by addition of a soluble charged polymer and a soluble neutral polymer. The charged polymer interacts with one fraction of polypeptides to form a precipitate. Neutral polymer enhances the effectiveness of the charged polymer in precipitating this fraction. By proper selection of the polymer combination, a desired polypeptide fraction can be precipitated from the solution while the other polypeptide fraction remains in solution or vice versa.

U.S. Pat. No. 4,716,219 discloses adsorbents for affinity chromatography of proteins consisting of an electroneutral carrier matrix, a spacer and a triazine coloring substance bonded to the amino group of the spacer.

In contradistinction to the above-described systems, it was desired to find a cost-effective system wherein the dyes could be easily bound to the polymeric phase, without having to carry out the chromatographic and solvent extractions necessary to form the covalent bond in the PEG/hydroxypropyl starch system of the prior art.

SUMMARY OF THE INVENTION

One aspect of this invention relates to a cost-effective aqueous two-phase partitioning system.

Another aspect of this invention also relates to an aqueous two-phase partitioning system which does not require repeated chromatographic and solvent extraction steps to bond the dyes to the phase-forming polymer.

Still another aspect of this invention also relates to a process for the separation of proteins, using aqueous two-phase partitioning.

The above and other aspects of this invention are obtained by using as the two-phase partitioning system one which has polyvinylpyrrolidone (PVP) rich phase as the lighter upper phase and maltodextrin as the heavier lower phase. This invention further takes advantage of the ability of polyvinylpyrrolidone to bond to triazine dyes in a noncovalent manner without diminishing the affinity effects of the dyes.

Upon further study of the specification and appended claims, further aspects and advantages of this invention will become apparent to those skilled in the art.

DETAILED DESCRIPTION OF THE INVENTION

Some proteins are known to interact specifically and strongly with textile triazine dyes. On the other hand, polyvinylpyrrolidone is also known to bind strongly with textile triazine dyes in a noncovalent manner without diminishing the affinity effects of the dyes.

It has been found that when appropriate concentrations of PVP and maltodextrin (a hydrolyzed corn starch product) are dissolved in aqueous solution, two phases form. The two phases which are characteristic of the system are an upper, PVP-rich phase and a lower, maltodextrin-rich phase which is practically devoid of PVP. Due to the relatively low cost of maltodextrin, this system provides for an effective two-phase system for partitioning proteins.

Further, when amino derivatives of textile triazine dyes are added to this system, they partition strongly into the PVP phase while retaining their ability to interact with soluble proteins. Thus, this system is appropriate for two-phase protein extraction. This system offers a simple, less expensive alternative to the prior art systems such as polyethylene glycol/dextran systems which employ dye-ligands that are covalently bonded to the PEG.

Further, the upper PVP-containing phase, either with or without dye, may be used as an extraction system.

The polyvinylpyrrolidone employed in the extraction system of the instant invention generally has an average molecular weight ($M_W$) of between 36,000 and 360,000, preferably about 360,000. The maltodextrins have molecular weights of between 600 and 5,000, preferably between 1,600 and 2,000. The phase systems are generally prepared at 4° C. using aqueous stock solutions of 20-25% polyvinylpyrrolidone and 33-40% maltodextrin. The final concentration of PVP in the upper phase is 3% to 15%, preferably 4% to 10%; and the final concentration of PVP in the lower phase is 0.05% to 1%, preferably 0.1% to 0.5%; the final concentration of maltodextrin in the upper phase is 15% to 20%, preferably 16% to 18%; and the final concentration of maltodextrin in the lower phase is 22% to 32%, preferably 23% to 28%.

The polyvinylpyrrolidone and maltodextrin system can be prepared by mixing the two aqueous solutions together at a temperature of 0°-8° C., preferably 2°-4° C. To ensure adequate contact and phase separation, it is preferred that the system is mixed vigorously for 1 to 2 minutes and then centrifuged. The pH of the system may have an effect on the ability of the dyes to extract protein into the upper phase. Preferably, a buffer is used to keep the pH of the system at 3 to 9, preferably 4.5 to 8. Buffers which may be used in the two-phase system of the instant invention include phosphate, acetic acid, Tris (tris(hydroxymethyl)aminomethane) and MES (2-[N-Morpholino]ethanesulfonic acid). A particularly preferred buffer is a mixture of acetic acid, MES and Tris.

The pH of the system can be adjusted by the addition of any suitable acid or base. Acids which may be used are any of the conventional acids, e.g., HCl and bases which may be used include any conventional base, e.g., NaOH.

The ionic strength of the system can also have an effect on the partitioning effect of certain proteins. The ionic strength can be varied by the addition of, e.g., NaCl. The addition of NaCl has been found to lower the partition coefficient of a system, e.g., decrease the ability to extract the protein into the upper phase.

The dyes which may be used to bind to the PVP phase are any amino derivatives of triazine dyes which will bind with the polyvinylpyrrolidone phase and still maintain their ability to interact with the protein to be separated. These include, but are not limited to, Cibacron Blue FGF, Procion Turquoise H-A, Procion Green HE-4BDA. The choice of dye will depend on the protein to be separated. It has been found that Procion Red HE-3B is particularly effective for the separation of alcohol dehydrogenase (ADH).

When used, the dye can be added to the system in a dye/PVP weight ratio of 0.005-10, preferably 0.01 to 0.4.

The amino derivative of a triazine dye can be produced by conventional techniques, e.g., by dissolving the dye in methanol, and adding concentrated ammonium hydroxide and refluxing. The remaining solvent can be removed, if necessary, by, e.g., evaporating, and washing the remaining solid and drying if necessary.

The protein separation according to the instant invention is carried out by adding the protein or mixture of proteins to be separated to the two-phase PVP/maltodextrin system to which the dye has been added. The protein is added to the system and then centrifuged to attain phase separation. The system should be operated at a temperature of 2°-6° C. The protein to be separated can be added in an amount of 0.01% to 10%. The dye, which partitions strongly into the upper, PVP-containing phase acts as a ligand for certain classes of proteins, thus extracting them from the lower phase. The protein-containing, upper, PVP-containing phase is then removed from the system, e.g., by a pipette, where it can undergo further purification. The protein is released from its dye-complex by increasing the ionic strength or pH of the upper-phase solution.

The proteins which can be extracted with this system are any protein which will bind to an amino derivative of the dye being utilized. These include, but are not limited to, the separation of ADH from a yeast cell homogenate and bovine serum albumin from whole serum.

BRIEF DESCRIPTION OF THE DRAWINGS

Various other objects, features and attendant advantages of the present invention will be more fully appreciated as the same becomes better understood when considered in conjunction with the accompanying drawings in which like reference characters designate the same or similar parts throughout the several views, and wherein.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire texts of all application, patents and publications, cited above and below, are hereby incorporated by reference.

EXAMPLES

Formation of Polyvinylpyrrolidone/Maltodextrin System

Polyvinylpyrrolidone, average molecular weight 360,000 (PVP 360) is used as the top phase-forming polymer. A maltodextrin derived from corn starch with a molecular weight of 1,800 (M100) is used as the lower phase-forming polymer. This polymer is available, inter alia, from Grain Processing Corporation. (Muscatine, IA). Phase systems are prepared from aqueous stock solutions of 20-25% (w/w) PVP 360 and 33-40% (w/w) M100. The PVP 360 and M100 concentrations in each phase were determined by a combination of refractometry and polarimetry using the method described by Bamberger et al. in "Partitioning in Aqueous Two-Phase Systems," pp. 85-130, Academic Press, Inc., New York (1985), for PEG/dextran two-phase systems. The specific rotation of M100 was found to be about $172° \, (gm/ml)^{-1} dm^{-1}$.

Figure 1:
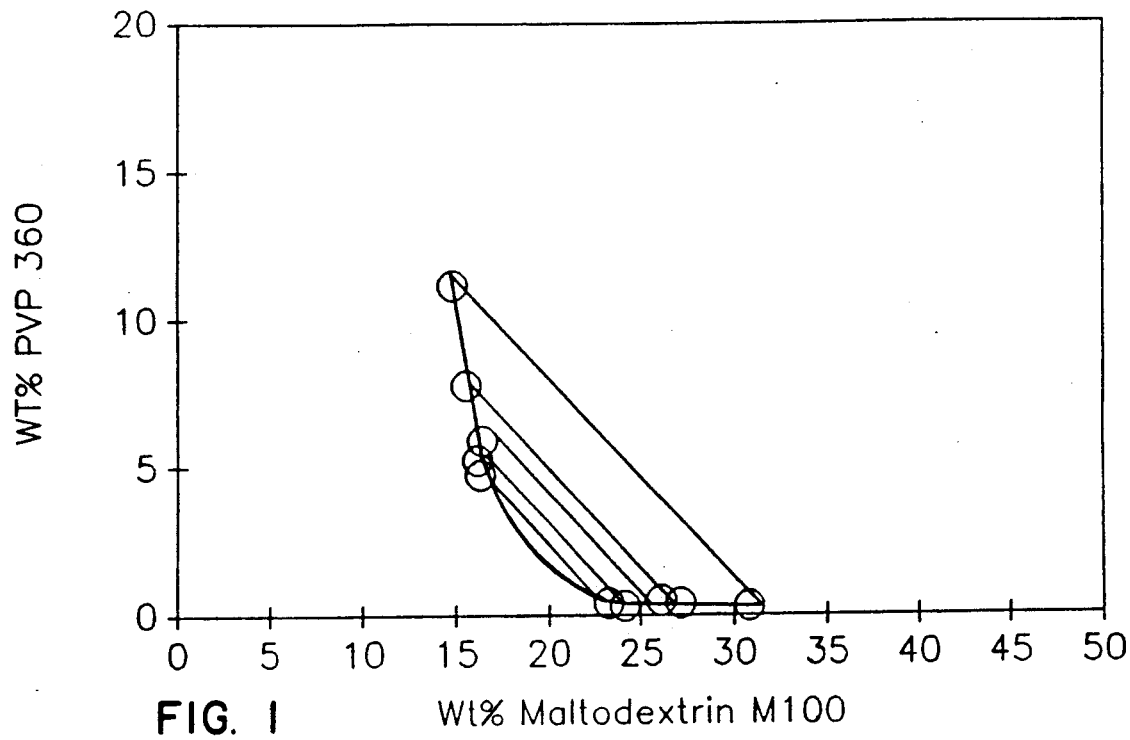
FIG. 1 depicts a phase diagram for a polyvinylpyrrolidone/maltodextrin system at 4° C.

The concentrations of PVP 360 and M100 in aqueous solution formed two phases at 4° C. It will also form two phases at higher temperatures, i.e., 25° C. The phase diagram will be shifted to the right, however. The phase diagram is shown in FIG. 1. Phase diagrams were determined from five 10 g total mass PVP 360/M100 systems which were mixed and equilibrated at 4° C. As can be seen in the diagram, the maltodextrin was much more soluble in the PVP 360 phase than was PVP 360 in the M100 phase.

Formation of Amino-Derivative of a Chlorotriazine Dye

The amino derivative of a chlorotriazine dye was formed as follows: 8 grams of the dye were dissolved in 50 ml methanol. 20 ml of concentrated ammonium hydroxide was added to this solution and refluxed for 30 minutes. The solvent was removed via rotary evaporation at reduced pressure. The remaining solid was washed with 500 ml acetone and dried before use in two-phase aqueous systems. Other dye ligands are produced in a similar manner.

Formation of Protein Mixtures

Yeast homogenate was prepared by grinding 5 g dried Bakers yeast with 25 g dry ice with a mortar and pestle for 5 minutes. The resulting paste was taken up in 50 ml water and kept on ice for immediate use or frozen at −20° C. for future use. The specific activity of ADH in mixtures of this type was between 5-10 U/mg protein when measured using the activity assay of Vallee and Hock, Proc. Nat'l Acad. Sci. (USA) 41, 327-330 (1955). Total protein was determined using duplicate samples with the Coomassie Blue dye-binding assay with egg white lysozyme as a standard. For two-phase systems containing textile dyes, an identical system with no protein served as a control for the total protein assay. Stock solutions of YEC were made at 10 mg/ml in water immediately before use. The specific activity of ADH in this soluble mixture was 17 U/mg protein.

Partitioning Experiments

For partitioning experiments, duplicates of phase systems were composed of 17% (w/w) M100 and 4.0% (w/w) PVP 360 in Buffer A at 4° C. Buffer A stock solution was a mixture of acetic acid, MES, and Tris all at a concentration of 500 mM. This stock solution was added to the phase systems such that the final concentration of each of the buffering species was 10 mM. The pH of the system was adjusted by the addition of dilute solutions of HCl or NaOH before it was brought to its final mass of 10 g. Systems were mixed vigorously for 1 minute before centrifugation at $4000 \times g_{avg}$ for 15 minutes at 4° C. to separate the phases. The top phase was carefully removed with a pipette. The bottom phase was recovered when needed by puncturing the 15 ml polypropylene tube at the tip to allow the phase to drain.

Measurement of Protein Partition

The partition coefficient (K) was used to describe the partition of purified ADH in the two-phase system. It is defined as the number of ADH activity units per ml in the upper phase divided by the number of ADH activity units per ml in the lower phase. To describe the affinity-partitioning effect that the dyes had on purified ADH, a value for Δ log K was determined. Δ log K can be defined as the increase in logarithmic partition coefficient of an enzyme caused by introducing a ligand into the system $$\Delta \log K = \log K \text{ (with ligand)} - \log K \text{ (without ligand)}$$

To describe the partition coefficient of both ADH and total protein in these systems, a relative partition coefficient (not a true partition coefficient in the thermodynamic sense), $K_u$ was used which includes protein losses due to denaturation or precipitation and the relative volumes of top and bottom phases. $K_u$ is defined as the total number of ADH activity units or mg total protein in the upper phase divided by the total ADH activity units or mg protein in the lower phase.

The partition fraction ($K_f$) is used to determine separation efficiency in phase systems which contain particulate material. The yeast cell homogenate used in some of the trials formed a pellet during centrifugation, thus yielding three phases which did not allow one to determine a value of K for the system. $K_f$ is defined as the concentration of ADH activity or protein in the top phase divided by the corresponding concentration in the total system control. Before centrifugation, 1 g of mixed system is removed and serves as the total system control when it is remixed and assayed for both ADH activity and protein concentration.

ADH activity yield can be defined in a similar manner. It is first calculated as the number of activity units in the upper phase divided by the number of activity units in the total system control. The resulting quotient is multiplied by 100 to obtain a value for percent yield.

Protein Partitioning Experiments

In some trials, the two-phase system was used to extract ADH from a yeast cell homogenate. As discussed above, the use of the homogenate prevented the direct measurement of the partition coefficient K due to the pelleted cellular debris which occupied a large fraction of the bottom phase. The pellet contained 60-70% of the total ADH activity, indicating the cell homogenization process did not effectively solubilize ADH activity or that the cell debris were acting as ion exchange. This means that the PVP/maltodextrin system partitioned the soluble ADH activity to a large extent in the upper phase. Defining a partition fraction $K_f$, as discussed above, allows measurement of the affinity effects of textile dyes added to the system.

Figure 2:
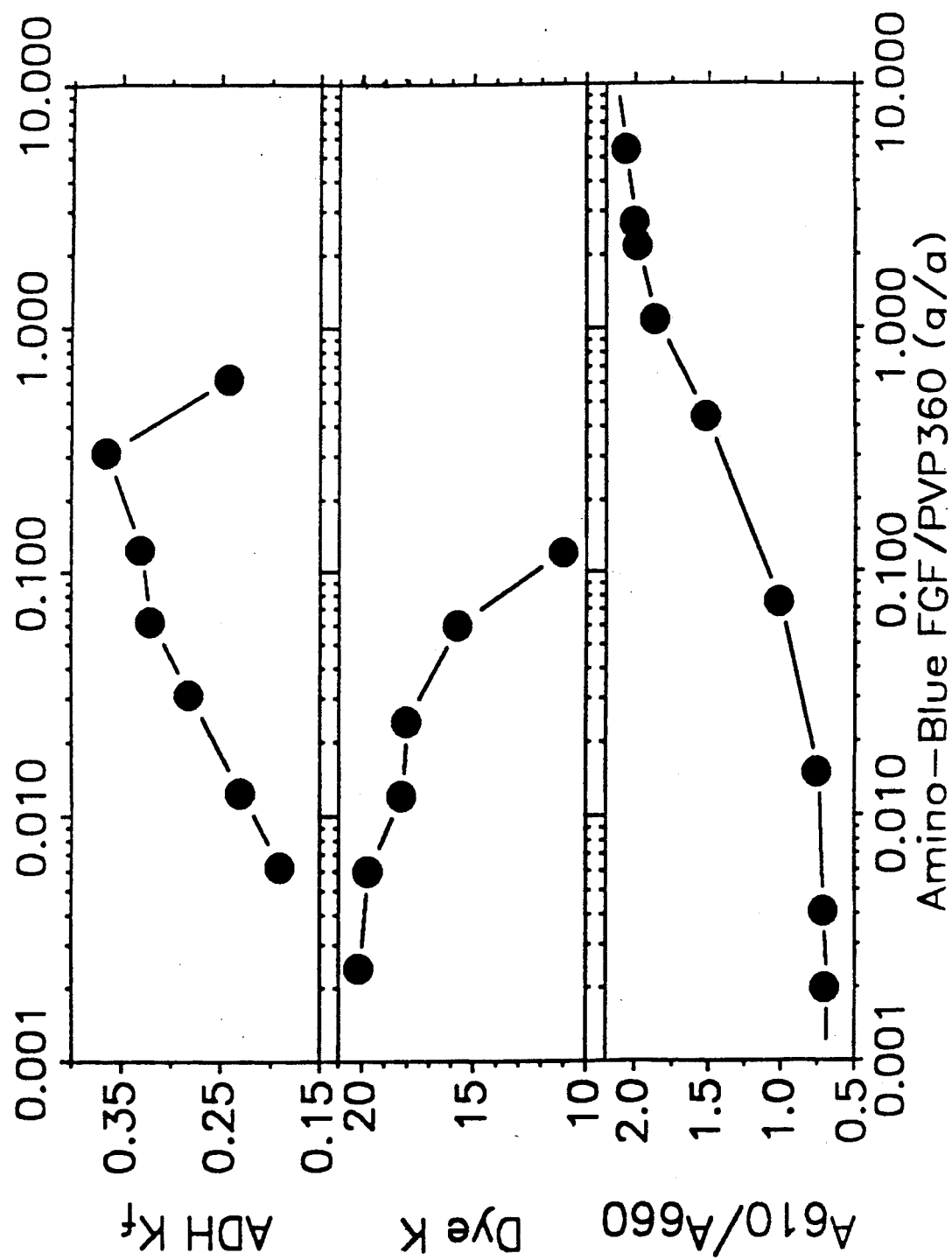
FIG. 2 shows the dye and protein interactions in a 4.0% (w/w) polyvinylpyrrolidone/buffer system at pH 4.5 and 4° C.

The dye and protein interactions in a 4.0% (w/w) PVP/17% maltodextrin/buffer system at a pH of 4.5 and 4° C. are shown in FIG. 2. The lower panel depicts the interaction in the amino derivative of Cibacron Blue FGF measured spectrophotometrically as the ratio of $A_{610}/A_{660}$. The middle panel indicates that the partition coefficient of Cibacron Blue, as measured spectrophotometrically, decreased nonlinearly as the dye/polyvinylpyrrolidone weight ratio increased. The results in the upper panel indicate that the partition fraction of ADH from a yeast cell homogenate reached a maximum when the PVP was approximately 50% saturated with dye. The $K_f$ value in the absence of dye was 0.151.

Dye Screening Experiments of Purified Alcohol Dehydrogenase (ADH)

Figure 3:
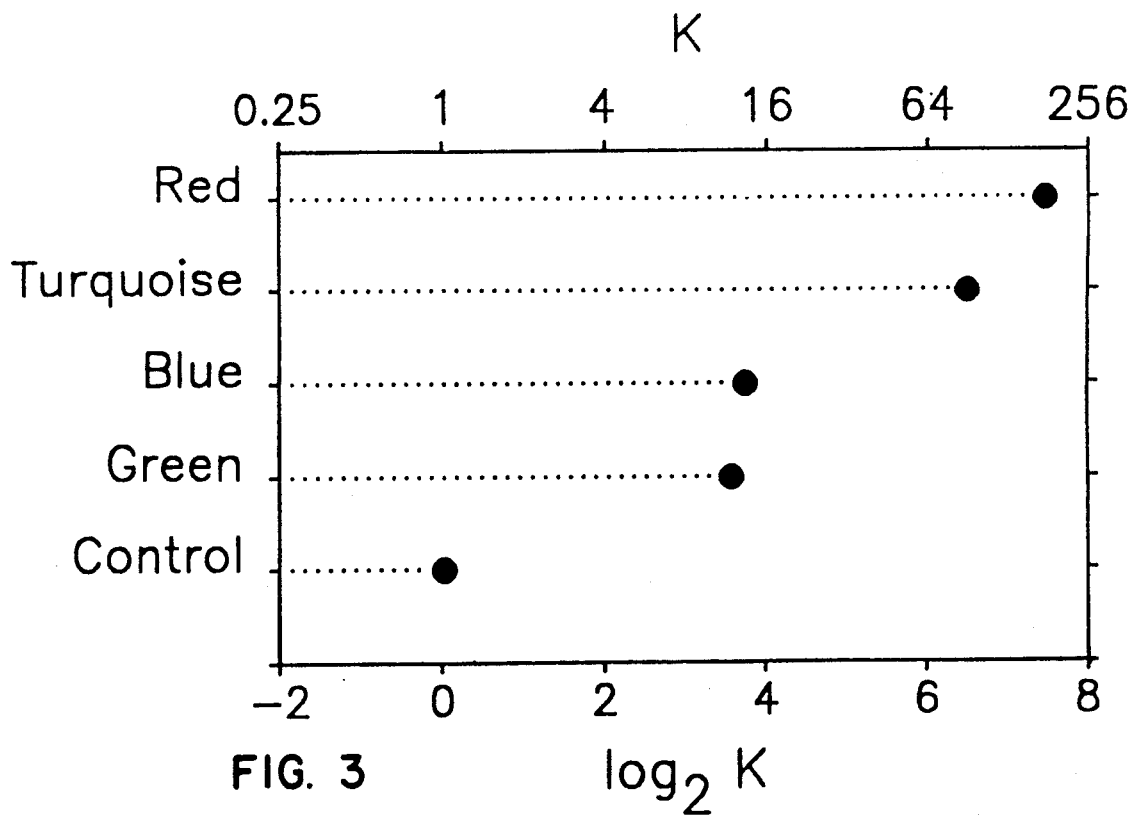
FIG. 3 depicts the dye screening of purified ADH in a 4.0% (w/w) polyvinylpyrrolidone/maltodextrin/buffer A system at pH 4.5 and 4° C.

Dye screening of purified ADH in a 4.0% (w/w) PVP 360/17% (w/w) M100/Buffer A system at pH 4.5 and 4° C. is presented in FIG. 3. Purified ADH (1.5 mg/10 g system) was partitioned in systems either lacking dye (designated as the control), or in the presence of the amino-derivative of four textile dyes at a final concentration of 0.1% each. The data indicates that Procion Red HE-3B (Red) gave the largest enhancement followed by Procion Turquoise H-A (Turquoise), Cibacron Blue FGP (Blue), and Procion Green HE-4BDA (Green).

Determination of the Effect of Ionic Strength on Separation

Figure 4:
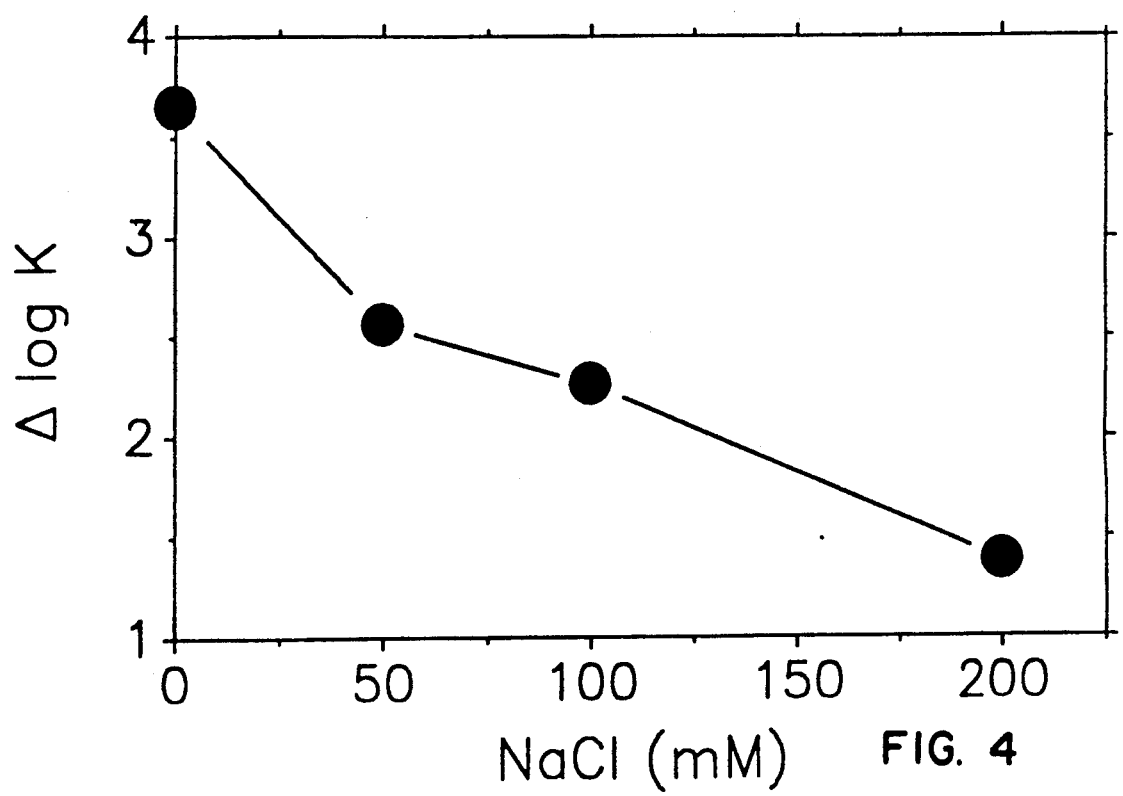
FIG. 4 depicts the effect of the ionic strength on the affinity partition of purified ADH.

The addition of varying amounts of NaCl to a polyvinylpyrrolidone/maltodextrin two-phase system containing 0.2% w/w of the amino-derivative of Procion Red HE-3B in the separation of purified ADH (1.5 mg/UG system) is shown in FIG. 4. It can be seen that the addition of NaCl decreases the ability of the dye to extract ADH in the upper phase. At the highest concentration of NaCl tested (200 mM), the system still maintained a Δ log K greater than 1.

Determination of the Effect of pH on Protein Separation

Figure 5:
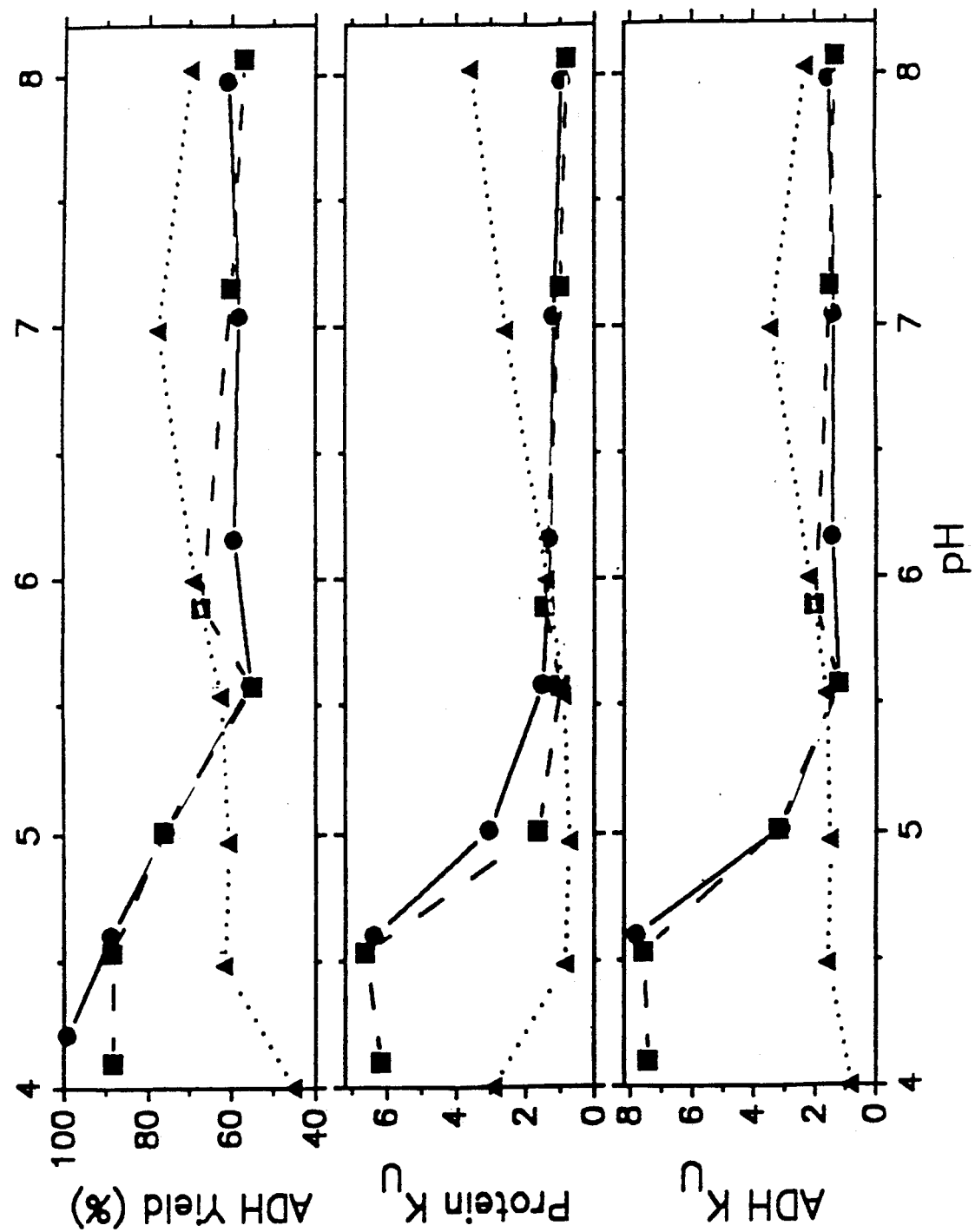
FIG. 5 shows the effects of pH on the partition of ADH and total protein from a soluble yeast enzyme concentrate.

The effects of pH on the partition of ADH and total protein from a soluble yeast concentrate are shown in FIG. 5. Yeast enzyme concentrate (0.1% (w/w) final concentration) was added to a 4.0% (w/w) PVP 360/17% (w/w) M100/Buffer A system at 4° C. and various pH values. Either no dye (▲), the amino derivative of Procion Red HE-3B (○; 0.1% (w/w)), or Cibacron Blue FGF (■; 0.1% (w/w)).

The $K_u$ values for ADH activity are shown as a function of system pH in the lower panel of FIG. 5. A $K_u$ value of 150 in the presence of the amino-derivative of Procion Red HE-3B at pH 4.21 was omitted to improve clarity.

The $K_u$ values for total protein are shown as a function of system pH in the middle panel of FIG. 5. A $K_u$ value of 133 in the presence of the amino-derivative of Procion Red HE-3B at pH 4.21 was omitted to improve clarity.

The upper panel of FIG. 5 depicts the yield of ADH activity as a function of system pH. In the figure, it can be seen that ADH from a soluble yeast enzyme concentrate had a maximum purification of 1.5-fold with a $K_u$ of 7.5 in a system containing the amino-derivative of Cibacron Blue FGF at a pH of 4.5 with a yield of 88%. In the absence of a dye, the ADH had a maximum $K_u$ of 3.4 at a pH of 7.0 with a yield of 75% and a purification of <1. The effects of the dyes were the most pronounced at pH values of less than 5. At higher pH values, the control system extracted more ADH activity as well as more total protein into the upper phase than did the dye-containing system.

Determination of the Effect of Amount of Protein Added

Figure 6:
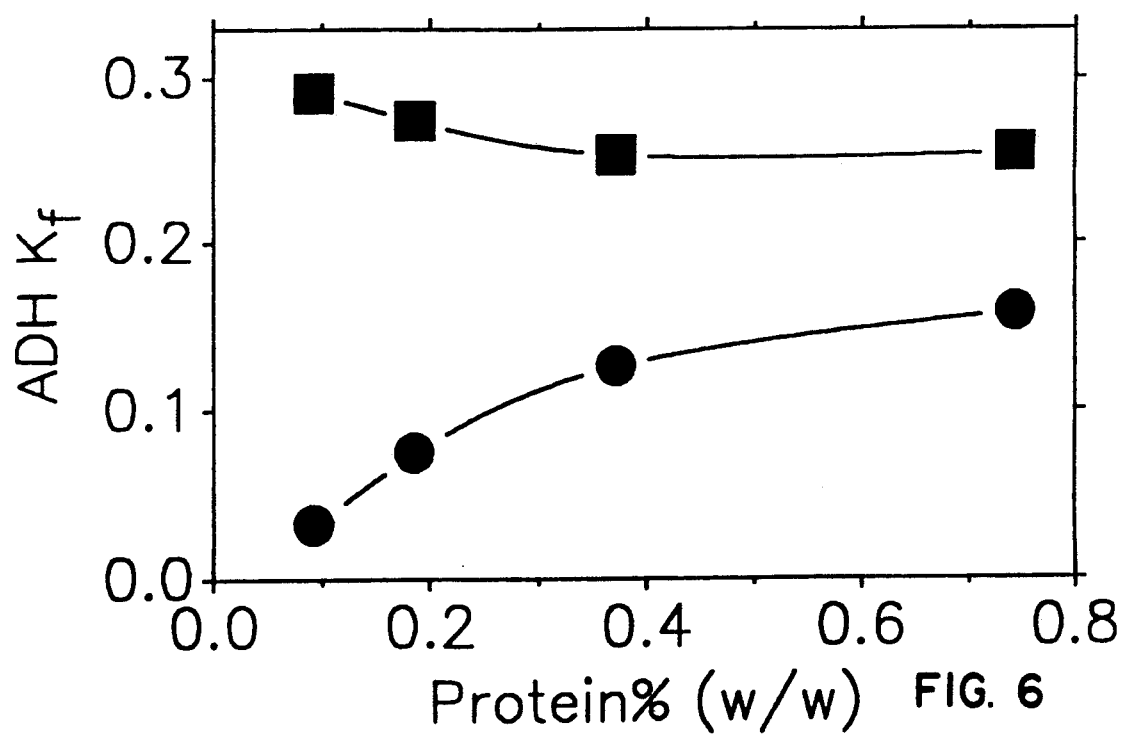
FIG. 6 depicts the effect of the amount of protein added to a polyvinylpyrrolidone/maltodextrin/buffer/Amino-Blue FGF system at pH 4.6 and 4° C.

Affinity partition of ADH from a yeast cell homogenate in a 4.0% (w/w) PVP 360/17% (w/w) M100/Buffer A/0.2% (w/w) Amino-Blue FGF system at pH 4.6 and 4° C. The partition fraction of ADH activity was measured as a function of the amount of protein added to the system from a yeast cell homogenate in either the absence (○) or presence (■) of the amino-derivative of Cibacron Blue FGF. The results are shown in FIG. 6. The results show that in a PVP/M100 system containing the amino-derivative of Cibacron Blue FGP showed a small decrease in the ability to extract ADH from a yeast cell homogenate as the amount of protein added to the system increased. The control system showed a 5-fold increase in the $K_f$ value for ADH as the protein concentration increased over the same range.

The preceding examples can be repeated with similar success by substituting the generically or specifically described teachings of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A two-phase aqueous protein extraction system containing polyvinylpyrrolidone, maltodextrin and an amino derivative of a triazine dye, comprising a lighter phase and a heavier phase, wherein the lighter phase comprises maltodextrin and polyvinylpyrrolidone and the heavier phase comprises maltodextrin and essentially no polyvinylpyrrolidone, wherein the amino derivative of the dye is non-covalently bonded to the polyvinylpyrrolidone-containing phase, said phases being in contact with each other, and wherein the protein being extracted binds to the amino derivative of the dye.

2. A system as claimed in claim 1, wherein the polyvinylpyrrolidone has a molecular weight of 36,000 to 360,000.

3. A system according to claim 1, wherein the dye employed is the amino derivative of Cibacron Blue FGF, Procion Turquoise H-A or Procion Green HE-4BDA.

4. A system according to claim 1, further comprising a buffer to maintain a pH of 3 to 9.

5. A system according to claim 4, wherein the buffer is a mixture of acetic acid, 2-[N-morpholino[ethanesulfonic acid and tris(hydroxymethyl)aminomethane.

6. A system according to claim 4, wherein the pH is 4.5 to 8.

7. In a method of partitioning proteins with a two-phase aqueous extraction system, the improvement which comprises using the two-phase system of claim 1.

8. A method according to claim 7, wherein the protein to be partitioned is alcohol dehydrogenase.

9. A two-phase extraction system comprising the composition set forth in the phase diagram of FIG. 1, and further comprising an amino derivative of a triazine dye which is non-covalently bonded to the polyvinylpyrrolidone-containing phase.

* * * * *